(12) United States Patent
Amisar

(10) Patent No.: US 7,846,740 B2
(45) Date of Patent: Dec. 7, 2010

(54) METHOD AND KIT FOR DETECTING EXPLOSIVE SUBSTANCES CONTAINING CERTAIN OXIDANTS

(75) Inventor: Shai Amisar, Tel Aviv (IL)

(73) Assignee: Mistral Detection Ltd., Herzliya Pitauch (IL)

( * ) Notice: Subject to any disclaimer, the term of this patent is extended or adjusted under 35 U.S.C. 154(b) by 1104 days.

(21) Appl. No.: 10/592,715

(22) PCT Filed: Feb. 2, 2005

(86) PCT No.: PCT/IL2005/000121

§ 371 (c)(1),
(2), (4) Date: Sep. 13, 2006

(87) PCT Pub. No.: WO2005/089058

PCT Pub. Date: Sep. 29, 2005

(65) Prior Publication Data

US 2008/0182334 A1 Jul. 31, 2008

(30) Foreign Application Priority Data

Mar. 21, 2004 (IL) .................................. 160989

(51) Int. Cl.
*G01N 21/00* (2006.01)
*G01N 21/75* (2006.01)
*G01N 33/00* (2006.01)
*G01N 15/06* (2006.01)
*G01N 33/48* (2006.01)
*B01L 3/00* (2006.01)

(52) U.S. Cl. ..................... 436/164; 436/110; 436/135; 422/61; 422/68.1

(58) Field of Classification Search ...................... None
See application file for complete search history.

(56) References Cited

U.S. PATENT DOCUMENTS

| | | | |
|---|---|---|---|
| 4,788,039 A | 11/1988 | Glattstein | |
| 5,296,380 A | 3/1994 | Margalit | |
| 5,332,662 A * | 7/1994 | Ullman | 435/28 |
| 5,480,612 A | 1/1996 | Margalit | |
| 5,648,047 A | 7/1997 | Kardish et al. | |
| 7,410,612 B1 * | 8/2008 | Carrington | 422/61 |
| 2004/0048329 A1 * | 3/2004 | Beuermann et al. | 435/28 |

FOREIGN PATENT DOCUMENTS

WO WO9943846 9/1999

* cited by examiner

*Primary Examiner*—Jill Warden
*Assistant Examiner*—Charles Hammond
(74) *Attorney, Agent, or Firm*—Frank H. Foster; Kremblas & Foster

(57) ABSTRACT

The invention relates to a method for detecting an explosive substance which contains chlorate, bromate and/or organic peroxide, wherein a suspect substance is contacted with a first reagent, which is a strongly acid solution of at least one primary or secondary aromatic amine, whereby chlorate or bromate type explosive affords a distinct coloration; and in the absence of such coloration, contacting the same sample (in contact with the first reagent) with a second reagent, which is a solution comprising cations of at least one transition metal, whereby the presence of organic peroxides in the sample, which has been hydrolyzed at least partly to hydrogen peroxide by the strong acid of the first reagent, affords a distinct coloration. The invention further relates to a kit containing separate first and second reagents; a container of mixed reagents for detecting peroxide; and a kit including such container.

7 Claims, No Drawings

METHOD AND KIT FOR DETECTING EXPLOSIVE SUBSTANCES CONTAINING CERTAIN OXIDANTS

FIELD AND BACKGROUND OF THE INVENTION

The present invention relates to an improved method and kit for detecting explosives selected from peroxides, chlorates and bromates.

In recent times, the use of home-made, improvised explosives has been growing rapidly, and peroxide based explosives, like triacetonetriperoxide (TATP) and hexamethylenetriperoxidediamine (HMTD), have been shown to be easily manufactured and almost as strong as the standard explosives used today.

Methods and tests kits for detecting explosives selected from nitroaromatics, organic nitrates, nitramines, inorganic nitrates, chlorates and bromates, have been described by Margalit in U.S. Pat. Nos. 5,296,380 and 5,480,612. Neither of these patents describe detection of peroxide based explosives. The entire contents of U.S. Pat. Nos. 5,296,380 and 5,480,612 are incorporated by reference herein.

Itzhaky et al., in WO9943846, has described a method and kit for detecting an organic peroxide-based explosive in a sample. The organic peroxide is hydrolyzed with strong acid to release hydrogen peroxide, and the resulting mixture is reacted with a peroxidase enzyme and a substrate capable of being oxidized by the oxidant under the catalysis of the enzyme to produce a pronounced change in a measurable physical parameter of the substrate. The entire contents of WO9943846 are incorporated by reference herein.

It is a principal object of the present invention to enable the detection of explosives containing chlorates or bromates, and the sequential detection of peroxide based explosives after testing for the presence of chlorates or bromates in the same sample. Other objects of the invention will be apparent from the description which follows.

SUMMARY OF THE INVENTION

The present invention accordingly provides in one aspect, a method for detecting an explosive substance which contains an oxidant selected from chlorate, bromate and organic peroxide, which method comprises the sequential steps of: providing a sample of suspect explosive substance; contacting the sample of said substance with a first reagent, which is a strongly acid solution of at least one primary or amine aromatic amine, whereby the presence of a chlorate or bromate type explosive affords a distinct coloration; and in the absence of such coloration, contacting the same sample, which is already in contact with the first reagent, with a second reagent, which is a solution comprising cations of at least one transition metal, whereby the presence of organic peroxides in the sample, which has been hydrolyzed at least partly to hydrogen peroxide by the strong acid of the first reagent, affords a distinct coloration.

In another aspect, the present invention provides a test kit for use in a method for detecting an explosive substance which contains an oxidant selected from chlorate, bromate and organic peroxide, which kit comprises the following components: a first container including therein a first reagent, which is a strongly acid solution of at least one primary or secondary aromatic amine; and a second container including therein a second reagent, which is a solution comprising cations of at least one transition metal.

In still another aspect, the invention provides a reagent kit for detecting an explosive substance which may contain an organic peroxide, which kit comprises a container of reagent which is a solution comprising cations of at least one transition metal, together with instructions for use in detection of said explosive after at least partial acid hydrolysis of the organic peroxide to hydrogen peroxide.

DETAILED DESCRIPTION OF THE INVENTION

In the method and test kit of the invention:

(a) at least one of the first and second reagents preferably includes at least one water-miscible non-aqueous solvent, such as at least one solvent selected from the group consisting of dimethyl sulfoxide, dimethylformamide, dimethylacetamide, hexamethylphosphoramide, N-methylpyrrolidone and water-miscible alcohols and ethers; and/or (b) the at least one primary or secondary aromatic amine preferably comprises a secondary aromatic amine such as a diarylamine, e.g. the carbocyclic secondary aromatic amine diphenylamine; and/or (c) the strong acid of the first reagent preferably comprises sulfuric acid, and may consist essentially of sulfuric acid; and/or (d) the at least one transition metal is preferably selected from iron (e.g. as $Fe^{+++}$), copper, manganese, chromium, cobalt and ruthenium;

(e) in absence of a positive coloration indicating the presence of chlorate, bromate or peroxide, the method includes preferably providing a second sample of said suspect substance, and testing it for at least one ingredient selected from nitroaromatics, organic nitrates, nitramines, and inorganic nitrates, while the kit preferably includes at least one container of reagent adapted for testing for the presence of the at least one ingredient.

In addition, the test kit of the invention preferably comprises at least one integral or discrete device for dispensing at least one of the first and second reagents, such as a spray or a dropping device.

Moreover, the test kit of the invention preferably comprises an absorbent medium (such as absorbent paper) for sampling a suspected source for explosives wherein said suspected source includes a substance, a surface of an inanimate object and an exterior periphery of a human.

It will be appreciated that the reagent kit according to the invention may also include the above-described preferred features, so far as may be desired or appropriate.

In a presently preferred embodiment of the kit of the invention, each of the first and second reagents are separately contained in closed plastic dropper bottles adapted for dispensing each of the components in a dropwise manner. Also in a particular embodiment, every pair of dropper bottle and cap is identified by a color mark which is different for each dropper bottle and its cap, thus enabling the user to match the correct bottle and cap.

While use of a secondary amine, and in particular, diphenylamine, is presently preferred because this is much less toxic and more sensitive for present purposes than aniline, nevertheless, use of a primary amine such as aniline is also within the scope of the present invention.

In a presently preferred embodiment of the invention, preparation of the test reagents may be carried out as follows.

Reagent A (For Chlorates or Bromates)

A liquid mixture is first prepared by carefully adding 95% sulfuric acid (400 ml) to a mixture of DMSO (90 ml), ethanol (100 ml) and water (500 ml). Diphenylamine (11 g) is then added to the liquid mixture, with stirring, until a homogeneous solution is obtained. The thus-prepared reagent is poured into a storage vessel prior to being used for filling ampoules. It is very stable under exposure to light and normal conditions; the ampoules do not need to be colored. This reagent gives a deep blue coloration with chlorates or bromates within 1-2 seconds, which fades on standing; it is sensitive to as little as 0.0000001 g/mm$^2$ of chlorate or bromate; perchlorate does not give a positive reaction.

Reagent B (For Organic Peroxide)

This is a solution of 1% FeCl$_3$ in dipropyleneglycol dimethyl ether. The sensitivity of this reagent is similar to that of reagent A, above.

Procedure

When a drop of reagent A is placed on a collecting medium, e.g. a filter paper, a polyethylene laminated paper, or one of these printed with a tacky layer of acrylate glue to enhance collection of particles, the presence of chlorates or bromates is indicated by a deep blue color. In the absence of color, a drop of reagent B is placed on the same paper. Development of a blue color at this stage will indicate the presence of organic peroxide in the original sample.

This system enables the operator to improve detection capability, by using only one collecting medium for both tests carried out sequentially.

While particular embodiments of the invention have been particularly described hereinabove, it will be appreciated that the present invention is not limited thereto, since as will be readily apparent to skilled persons, many modifications or variations can be made. Such modifications or variations which have not been detailed herein are deemed to be obvious equivalents of the present invention.

The invention claimed is:

1. A method for detecting an explosive substance which contains an oxidant selected from chlorate, bromate and organic peroxide, which method comprises the sequential steps of:
   providing a sample of suspect explosive substance;
   contacting the sample of said substance with a first reagent, which is a strongly acidic solution of at least one primary or secondary aromatic amine, whereby the presence of a chlorate or bromate type explosive affords a distinct coloration; and in the absence of such coloration,
   contacting the same sample, which is already in contact with the first reagent, with a second reagent, which is a solution comprising cations of at least one transition metal, whereby the presence of organic peroxides in the sample, which has been hydrolyzed at least partly to hydrogen peroxide by the strong acid of the first reagent, affords a distinct coloration.

2. A method according to claim 1, which is further characterized by at least one of the following features:
   (a) at least one of said first and second reagents includes at least one water-miscible non-aqueous solvent;
   (b) said at least one primary or secondary aromatic amine comprises a carbocyclic secondary aromatic amine;
   (c) said strong acid of said first reagent comprises sulfuric acid;
   (d) said at least one transition metal is selected from iron, copper, manganese, chromium, cobalt and ruthenium;
   (e) in absence of a positive coloration indicating the presence of chlorate, bromate or peroxide, providing a second sample of said suspect substance, and testing it for at least one ingredient selected from nitroaromatics, organic nitrates, nitramines, inorganic nitrates.

3. A method according to claim 2, which is further characterized by at least one of the following features:
   (a) at least one of said first and second reagents includes at least one water-miscible non-aqueous solvent selected from the group consisting of dimethyl sulfoxide, dimethylformamide, dimethylacetamide, hexamethylphosphoramide, N-methylpyrrolidone and water-miscible alcohols and ethers;
   (b) said at least one primary or secondary aromatic amine comprises a diarylamine;
   (c) said strong acid of said first reagent consists essentially of sulfuric acid;
   (d) said cations comprise Fe$^{+++}$ ions.

4. A method according to claim 2, wherein said secondary aromatic amine is diphenylamine.

5. A test kit for use in a method for detecting an explosive substance in a suspect sample which contains an oxidant selected from chlorate, bromate and organic peroxide, wherein said kit comprises the following components:
   a first container including therein a first reagent, which is a strongly acidic solution of at least one primary or secondary aromatic amine; and
   a second container including therein a second reagent, which is a solution comprising cations of at least one transition metal, and
   which is further characterized by the following features:
   (a) at least one of said first and second reagents includes at least one water-miscible non-aqueous solvent;
   (b) said at least one primary or secondary aromatic amine comprises a carbocyclic aromatic amine;
   (c) said strongly acidic solution of said first reagent comprises sulfuric acid;
   (d) said at least one transition metal is selected from iron, copper, manganese, chromium, cobalt and ruthenium;
   (e) said kit comprises at least one integral or discrete device for dispensing at least one of said first and second reagents;
   (f) said kit comprises an absorbent medium for sampling a suspected source for explosives wherein said suspected source includes a substance, a surface of an inanimate object and an exterior periphery of a human; and
   (g) said kit includes additionally at least one container of reagent adapted for testing for the presence of at least one further ingredient in said suspect sample selected from nitroaromatics, organic nitrates, nitramines, inorganic nitrates.

6. A kit according to claim 5, which is further characterized by at least one of the following features:
   (a) at least one of said first and second reagents includes at least one water-miscible non-aqueous solvent selected from the group consisting of dimethyl sulfoxide, dimethylformamide, dimethylacetamide, hexamethylphosphoramide, N-methylpyrrolidone and water-miscible alcohols and ethers;
   (b) said at least one primary or secondary aromatic amine comprises a diarylamine;
   (c) said strongly acid solution of said first reagent consists essentially of sulfuric acid;
   (d) said cations comprise Fe$^{+++}$ ions;
   (e) said at least one device is selected from spray devices and dropping devices;
   (f) said absorbent medium is absorbent paper.

7. A kit according to claim 6, wherein said diarylamine is the carbocyclic secondary aromatic amine diphenylamine.

* * * * *